United States Patent [19]

Mross et al.

[11] 4,324,699

[45] Apr. 13, 1982

[54] SUPPORTED CATALYSTS AND THEIR TREATMENT FOR THE PREPARATION OF ETHYLENE OXIDE

[75] Inventors: Wolf D. Mross; Eckart Titzenthaler, both of Ludwigshafen; Juergen Koopmann, Neustadt; Volker Vogt, Wachenheim; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 115,732

[22] Filed: Jan. 28, 1980

[30] Foreign Application Priority Data

Feb. 9, 1979 [DE] Fed. Rep. of Germany ....... 2904919

[51] Int. Cl.³ .................... B01J 21/04; B01J 23/04; B01J 23/50
[52] U.S. Cl. .................... 252/463; 252/476; 260/348.34
[58] Field of Search .............. 252/476, 412, 414, 463; 260/348.34

[56] References Cited

U.S. PATENT DOCUMENTS 2,245,183  6/1941  Christ et al. ................ 252/476 X
4,123,385 10/1978  Rebsdat et al. ............. 252/463 X
4,125,480 11/1978  Maxwell ..................... 252/412 X
4,168,247  9/1979  Hayden et al. .............. 252/476

FOREIGN PATENT DOCUMENTS 867045 11/1978 Belgium.

Primary Examiner—W. J. Shine
Attorney, Agent, or Firm—John H. Shurtleff

[57] ABSTRACT

Supported catalysts containing silver and alkali metals, for the preparation of ethylene oxide from ethylene and oxygen in the gas phase, are prepared or regenerated by modifying, respectively, a new or spent supported catalyst which already contains metallic silver and may or may not contain the light alkali metals lithium and/or sodium and, where a spent catalyst is concerned, also contains the heavy alkali metals potassium, rubidium and/or cesium, with a solution containing the heavy alkali metals, the modifier solution used containing (a) a surfactant and/or a reducing agent, in the case of the preparation of a new catalyst or (b) a surfactant, in the case of the regeneration of a spent catalyst.

8 Claims, No Drawings

SUPPORTED CATALYSTS AND THEIR TREATMENT FOR THE PREPARATION OF ETHYLENE OXIDE

The present invention relates to a novel process for the preparation and regeneration of supported catalysts, containing silver and alkali metals, which catalysts exhibit improved efficiency when used for the preparation of ethylene oxide from ethylene and oxygen in the gas phase.

Apart from the improvement according to the invention, the above types of catalysts are generally known. They contain silver and alkali metals as the active component and are prepared, for example, by impregnating the carrier, for example alumina, with a solution containing silver and an alkali metal and then heating the impregnated material to convert the silver to the active metallic form.

German Published Application DAS No. 2,519,599 discloses that the efficiency of silver-containing catalysts for the preparation of ethylene oxide, which after prolonged use show diminished selectivity in respect of the formation of ethylene oxide, can be improved if a cation of a heavy alkali metal, eg. rubidium or especially cesium, is applied to the catalyst. According to U.S. Pat. No. 4,033,903, a similar improvement is achieved in the case of unspent, but thermally pretreated catalysts for the preparation of ethylene oxide. In the case of unspent, or not thermally pretreated, catalysts, subsequent modification with the heavy alkali metals, carried out in a conventional manner, however only slightly improves the selectivity. It is true that if the heavy alkali metals are applied to the carrier simultaneously with the silver, the selectivity is also improved, but this diminishes again relatively rapidly when the catalyst is used. The light alkali metals, which in the main serve to increase the life of the catalyst, ie. which prolong the full activity of the catalyst, can on the other hand be applied to the carrier together with the silver.

It is an object of the present invention to utilize the activating effect of the heavy alkali metals even for unspent catalysts and at the same time also to improve the effect of regeneration. This object has already been achieved satisfactorily by the methods of copending U.S. application Ser. No. 959,684, filed Nov. 13, 1978, now U.S. Pat. No. 4,278,562, wherein the heavy alkali metals are applied to the supported catalyst, which already contains silver and may or may not already contain the light alkali metals, by means of a solution of an oxygen-containing or nitrogen-containing compound which can form complex salts with Ag(I) ions.

In further pursuance of this general object, the specific object of the present invention is further to improve the modification of the catalyst with the heavy alkali metals, and hence the activity of the catalysts.

We have found that this object is achieved by a process for the preparation and regeneration of supported catalysts containing silver and alkali metals, for the preparation of ethylene oxide from ethylene and oxygen in the gas phase, by modifying a new or spent supported catalyst which already contains metallic siver and may or may not contain the light alkali metals lithium and/or sodium and, where a spent catalyst is concerned, also contains the heavy alkali metals potassium, rubidium and/or cesium, with a solution containing the heavy alkali metals, the modifier solution used containing (a) a surfactant and/or reducing agent, in the case of the preparation of a new catalyst or (b) a surfactant, in the case of the regeneration of a spent catalyst.

Further, we have found that the effect of the surfactant and/or reducing agent can be boosted if in either case (a) or case (b) the modifier solution additionally contains an oxygen-containing or nitrogen-containing compound which forms complex compounds with Ag(I) ions.

The process is based on the hypothesis (and observations associated therewith), that the activity of the catalyst is dependent on the feasibility of the spatial interaction between the metallic silver on the one hand and the alkali metal cations, on the other hand. Whilst in the case of the light alkali metals this interaction is evidently relatively insensitive to external factors, it presumably depends, in the case of the heavy alkali metals, on the fact that the heavy alkali metal cations only adhere to the metallic silver when they are very close thereto and when there are no longer silver cations present which, because of their naturally greater affinity for metallic silver, are responsible for a spatial separation between the alkali metal cations and the silver and hence for a reduction of the interaction. This is in accord with the measures proposed according to the invention, since the reducing agents and the complexing agents lower the Ag ion concentration and the surfactants result in improved wetting of the silver with the modifier solution.

Accordingly, the catalysts according to the invention are prepared in two stages, the first stage concerning the preparation of the basic catalyst I and the second the preparation of the finished, heavy alkali metal-modified catalyst II.

The basic catalyst is prepared in accordance with the prior art, i.e. the carrier is impregnated with a solution which contains silver salts and may or may not contain lithium salts and/or sodium salts, and the impregnated material is heated at 150°–300° C., whereby the silver is converted to the metallic form.

The basic catalyst preferably exhibits the characteristics shown in Table 1.

TABLE 1

| Composition of the basic catalyst I in % by weight | | |
|---|---|---|
| Carrier | about 88–98, | preferably 88–94% |
| Silver | about 2–12, | preferably 6–12% |
| $Li^+ + Na^+$ | 0.0005–0.03, | preferably 0.005–0.025% |
| $Li^+$ | 0.0005–0.025, | preferably 0.005–0.015% |
| $Na^+$ | 0.0015–0.035, | preferably 0.004–0.025% |
| Approximate atomic ratio: | | |
| $Ag:(Li^+ + Na^+)$ | 5:1–1,500:1, | preferably 15:1–150:1 |

Suitable carriers include silicates, quartz, silicon carbide and graphite, and especially α-alumina. As is generally the case for gas phase reactions of fixed bed catalysts, examples of suitable shapes of carrier are balls and especially rings of from 5 to 10 mm diameter.

The impregnation is preferably carried out with the silver in the form of amine complex salts in which the anion is nitrate, carbonate, hydroxide or a carboxylic acid anion. Examples of suitable amine components are alkylamines and hydroxyalkylamines of up to about 6 carbon atoms. Inter alia, the butylamines, and especially sec.-butylamine, have proved effective. The light alkali metals are preferably used in the form of salts with the above anions, and the solvent is preferably water.

The appropriate composition of the impregnating solution depends on the absorbency of the carrier and on the desired content of the active catalyst constituents in the finished catalyst, and can easily be determined by preliminary experiments. If necessary, the impregnation treatment can be repeated several times, in each case after intermediate drying. When the required amount of the active catalyst constituents has been applied to the carrier, the latter is heated to 150–300° C., in a conventional manner. Though in principle it would be advantageous to heat the material in a non-oxidizing atmosphere, heating is, for practical reasons, carried out in a stream of air, in particular since the after-treatment according to the invention ensures complete reduction of the silver. After this, the basic catalyst I is ready to use. The selectivities achievable with these catalysts, for an oxygen conversion of 50%, are as a rule from 65 to 75%.

If, in accordance with the invention, the catalyst I is additionally modified with 0.0005–0.025, preferably 0.005–0.025, % by weight, based on total amount of catalyst, of a heavy alkali metal, i.e. potassium and/or rubidium and/or especially cesium, an improvement in selectivity of up to about 15 percent (absolute) is achieved.

The measures proposed according to the invention produce a substantial improvement in selectivity of unspent catalysts I, and a corresponding improvement in respect of the high selectivities with spent catalysts I and II.

To prepare the modified catalysts II, conventional, preferably alcoholic, solutions of compounds of the heavy alkali metals are used to impregnate the catalyst I or the spent catalyst II. Preferred compounds to use are the hydroxides and nitrates, but the carbonates, and the salts of carboxylic acids, are also suitable. The $C_1$–$C_3$-alkanols are particularly suitable solvents.

The amount of solution required for the impregnating after-treatment of the catalysts I depends on the absorbency of the latter and is easily determined by preliminary experiments. In general, it is 100–500 ml per kilogram of catalyst. The content of heavy alkali metal cations in the solution is about 0.005–0.15, preferably 0.015–0.1, % by weight, the lower ranges of concentration applying to the case of a repeated regeneration, i.e. to cases where the catalyst to be treated already contains the heavy alkali metals.

The amount of the heavy alkali metals in the finished catalyst II is preferably 0.0005–0.025, especially 0.005–0.025, % by weight.

The surfactants to be used according to the invention exhibit their desired effect even at very low concentrations, but are in general used in concentrations of 0.01–10, preferably 0.1–5, % by weight of the impregnating solution.

In principle, any sulfur-free and halogen-free wetting agent may be used, but nonionic surfactants are preferred. These inter alia include the general category of polyglycol ethers (oxyethylation products) of aliphatic, cycloaliphatic and alkyl-aromatic alcohols, as well as esters of fatty acids and amides of fatty acids. Examples of suitable commercial surfactants are oleic acid ethanolamide, triethanolamine monostearate, the reaction product of nonylphenol with 14 moles of ethylene oxide and the reaction product of oleylamine with 12 moles of ethylene oxide.

The reducing agents used according to the invention serve to reduce silver cations. They are therefore employed in equivalent amount or slight excess relative to the amount of silver ion in the catalyst I. In general, the impregnating solution used contains 0.5 to 10% by weight of reducing agent. The Ag ion concentration in the catalyst can be determined by eluting the ions with water and then determining them titrimetrically.

Because of the ease with which silver ions can be reduced, virtually all reducing agents are suitable, with the exception of those which contain halogen or sulfur, since they can poison the catalyst. Examples of suitable reducing agents are hydrazine, hydroquinone, p-aminophenol, p-diaminobenzene and p-hydroxy-N-methylaniline.

In addition to the surfactants and/or reducing agents, it can be useful to employ compounds which form complexes with Ag(I) ions. Such complexing agents include, for example, diketones, e.g. diacetyl and acetylacetone, ethyl acetoacetate, multiple ethers, e.g. the crown ethers, ammonia, nitriles and amines, preferably aliphatic and cycloaliphatic amines. More specific examples of the nitrogen-containing complexing agents are acetonitrile, mono-, di- and tri-alkylamines and -alkanolamines of a total of up to 6 carbon atoms, ethylenediamine and piperazine.

The concentration of such complexing agents in the modifier solutions is advantageously 0.1–30, preferably 0.1–10, % by weight.

Modification with the solutions which contain the heavy alkali metals and the additives according to the invention is carried out in a conventional manner by impregnating the catalyst I. Where regeneration is concerned, the solutions are allowed to run over the fixed catalyst and the excess solvent is blown off, for example with nitrogen. The catalyst is then dried, after which it is gradually heated to 150°–300° C. under nitrogen. The treated catalyst is then ready to use.

The preparation of ethylene oxide from ethylene and oxygen in the gas phase is carried out under conventional conditions, i.e. using a molar ratio ethylene: $O_2$ of from 0.5:1 to 5:1, under a pressure of 1–50 bar, at from 150° to 350° C., in the presence or absence of inert gases and inhibitors. Further details are therefore not needed here, particularly since the preparation of the catalysts in accordance with the invention results in an improvement in every case.

The improvement is principally that the selectivity in respect of ethylene oxide is increased, regardless of whether light alkali metals are present or not. In most cases, the light alkali metals additionally increase the selectivity, but especially increase the life of the catalyst.

A further advantage of the catalysts II prepared in accordance with the invention, using reducing agents, is that the start-up stage of using the catalyst does not exhibit a pronounced activity maximum, in contrast to what is found with conventional catalysts. This means that the precise and difficult temperature control during the start-up stage, which is necessary to avoid an uncontrollable exothermic reaction, is superfluous or at least substantially easier.

EXAMPLE 1

Preparation of a basic catalyst I 1 kg of commercial α-alumina was impregnated with a solution of 120 g of sec.-butylamine, 29 g of water, 139 g of silver nitrate and 1.39 g of lithium nitrate and then dried in a through-circulation oven at 220° C. This catalyst contained 8.0% by weight of silver and 0.015% by weight of lithium (Li+).

The α-alumina, from Norton, type SA 5551, was in the form of rings (diameter 7.5 mm, thickness 2.5 mm) and had a water adsorption of 0.23 ml/g, a surface area of 0.23 m²/g and a bulk density of 1.1 g/ml.

EXAMPLE 2

Preparation of various catalysts II 100 g portions of the basic catalyst from Example 1 were impregnated with a solution of 16.2 g of methanol, 16.4 mg of cesium hydroxide and 0.5 g of a surfactant, and then dried in a through-circulation oven at 200° C. This catalyst contained 0.015% by weight of cesium (Cs+) in addition to the constituents of the basic catalyst.

Table 2 shows the nature of the surfactants employed.

EXAMPLE 3

Preparation of ethylene oxide

The catalysts from Examples 1 and 2 were comminuted to a particle size of from 0.5 to 0.6 mm and introduced into a test reactor (containing 5 g of catalyst). A gaseous mixture of 8% by volume of oxygen, 30% by volume of ethylene, 1 ppm of vinyl chloride, remainder nitrogen, was passed through this catalyst at 15 bar and T° C. The temperature T was selected to achieve an oxygen conversion of 50% in every case. The selectivities S in respect of ethylene oxide are shown in Table 2.

TABLE 2

| Experiment No. | Catalyst | Surfactant | T °C. | S % |
|---|---|---|---|---|
| 1 C+ | I. Ex. 1 | — | 218 | 72.0 |
| 2 C+ | II. Ex. 2 | — | 219 | 75.0 |
| 1 | II/1 | nonylphenyl + 14 ethylene oxide | 219 | 81.0 |
| 2 | II/2 | coconut fatty alcohol + 8 ethylene oxide | 218 | 81.5 |
| 3 | II/3 | nonylphenol + 8 ethylene oxide | 223 | 82.0 |
| 4 | II/4 | oleylamine + 12 ethylene oxide | 220 | 82.0 |
| 5 | II/5 | nonylphenol + 12 ethylene oxide | 221 | 81.5 |

TABLE 2-continued

| Experiment No. | Catalyst | Surfactant | T °C. | S % |
|---|---|---|---|---|
| 6 | II/6 | triethanolamine monostearate | 224 | 82.0 |
| 7 | II/7 | tallow alcohol + 20 ethylene oxide | 222 | 81.0 |
| 8 | II/8 | oleic acid ethanolamide | 221 | 82.0 |

+for comparison

EXAMPLE 4

Preparation of a basic catalyst I

This catalyst was prepared by the method described in Example 1, but was not dried for such a long period, so that only 88.7% of the Ag+ were reduced. The remainder was in the ionic form.

EXAMPLE 5

Preparation of various catalysts II 100 g portions of the basic catalyst of Example 4 were impregnated with a solution of 16.2 g of methanol, 16.4 mg of cesium hydroxide, 0.5 g of a reducing agent, 0.5 g of a surfactant (optional) and 0.5 g of a complexing agent (optional) and were then dried at 200° C. in a through-circulation oven. This catalyst contained 0.015% by weight of cesium (Cs+) in addition to the constituents of the basic catalyst.

The nature of the agents used is shown in Table 3.

EXAMPLE 6

Preparation of ethylene oxide

The preparation of the ethylene oxide was carried out with the catalysts of Example 5, by a method similar to that of Example 3.

The results are shown in Table 3, the surfactant being omitted in Experiments 1–8 and 10, and the complexing agent being omitted in Experiments 9, 11 and 12. In the Comparative Experiments IC and 2C, it was necessary to reduce the temperature by about 20° C. during the start-up stage, because of the activity maximum, and then to raise it again gradually. On the other hand, in Experiments 1 to 15, this measure was not necessary.

TABLE 3

| Experiment No. | Catalyst | Reducing agent | Surfactant | Complexing agent | T °C. | S % |
|---|---|---|---|---|---|---|
| IC+ | I. Ex. 4 | — | — | — | 218 | 69.0 |
| 2C+ | II. Ex. 5 | — | — | — | 218 | 71.0 |
| 1 | II/1++ | hydrazine | — | octylamine | 218 | 82.0 |
| 2 | II/2 | hydrazine | — | sec.-butylamine | 218 | 82.5 |
| 3 | II/3 | hydrazine | — | sec.-butylamine | 222 | 82.5 |
| 4 | II/4 | p-aminophenol | — | dodecylamine | 225 | 82.0 |
| 5 | II/5 | p-diaminobenzene | — | laurylamine | 223 | 81.5 |
| 6 | II/6 | p-N-methylaminophenol | — | sec.-butylamine | 222 | 82.0 |
| 7 | II/7 | p-phenyl-pyrazolid-3-one | — | propylamine | 225 | 81.5 |
| 8 | II/8 | H₂O₂ | — | sec.-butylamine | 221 | 80.0 |
| 9 | II/9 | p-diaminobenzene | nonylphenyl + 14 EO | — | 226 | 82.5 |
| 10 | II/10 | hydroquinone + p-aminophenol, 1:1 | — | sec.-butylamine | 222 | 82.5 |
| 11 | II/11 | hydrazine | nonylphenol + 8 EO | — | 222 | 82.0 |
| 12 | II/12 | hydrazine | nonylphenol + 12 EO | — | 225 | 82.5 |
| 13 | II/13 | hydrazine | nonylphenol + 8 EO | sec.-butylamine | 223 | 82.5 |
| 14 | II/14 | hydroquinone | oleic acid ethanolamide | octylamine | 224 | 82.5 |

TABLE 3-continued

| Experiment No. | Catalyst | Reducing agent | Surfactant | Complexing agent | T °C. | S % |
|---|---|---|---|---|---|---|
| 15 | II/15 | p-aminophenol | oleylamine + 12 EO | dodecylamine | 226 | 82.0 |

+ for comparison;
++ in each case using the method of Example 5;
EO = ethylene oxide

We claim:

1. A process for the treatment of supported catalysts containing silver and alkali metals, for the preparation of ethylene oxide from ethylene and oxygen in the gas phase, which process comprises modifying a new supported catalyst which already contains metallic silver and may or may not contain the light alkali metal lithium and/or sodium with a modifier solution containing at least one of the heavy alkali metals, potassium, rubidium and/or cesium, the modifier solution used also containing
    (a) a surfactant and/or
    (b) a reducing agent.

2. A process as claimed in claim 1, wherein an agent which forms complexes with Ag(I) ions is used additionally.

3. A process as claimed in claim 1 or 2, wherein the catalyst prepared has the following composition:
    about 88–98% by weight of carrier
    about 2–12% by weight of silver
    0.0005–0.03% by weight of lithium and/or sodium
    0.0005–0.025% by weight of potassium and/or rubidium and/or cesium.

4. A process as claimed in claim 1 wherein alumina is used as the carrier.

5. A process as claimed in claim 1 wherein the heavy alkali metal is cesium.

6. A modified catalyst as obtained by the process of claim 1 and containing lithium as the light alkali metal component.

7. A modified catalyst as obtained by the process of claim 2 and containing lithium as the light alkali metal component.

8. A modified catalyst as claimed in claim 6 or 7 having the following composition:
    (a) about 88–98% by weight of carrier;
    (b) about 2–12% by weight of silver;
    (c) about 0.0005–0.03% by weight of lithium and
    (d) about 0.0005–0.025% by weight of potassium and/or rubidium and/or cesium.

* * * * *